United States Patent [19]
Kerver et al.

[11] Patent Number: 5,964,787
[45] Date of Patent: Oct. 12, 1999

[54] STIMULUS SYSTEM WITH CONTROLLABLE SWITCHED CAPACITOR OUTPUT STAGE

[75] Inventors: Harry B. Kerver, Duiven; Bernardus F. M. Vonk, Wehl, both of Netherlands

[73] Assignee: Vitatron Medical B.V., Dieren, Netherlands

[21] Appl. No.: 09/061,982

[22] Filed: Apr. 17, 1998

[51] Int. Cl.⁶ .................................................. A61N 1/362
[52] U.S. Cl. .................................................................. 607/9
[58] Field of Search ............................. 607/5, 13, 9, 27, 607/28

[56] References Cited

U.S. PATENT DOCUMENTS

| | | |
|---|---|---|
| 4,343,312 | 8/1982 | Cals et al. . |
| 4,373,531 | 2/1983 | Wittkampf et al. . |
| 4,401,120 | 8/1983 | Hartlaub et al. . |
| 4,550,370 | 10/1985 | Baker ........................................ 364/413 |
| 4,556,063 | 12/1985 | Thompson et al. . |
| 4,768,512 | 9/1988 | Imran . |
| 4,821,724 | 4/1989 | Whigham et al. . |
| 4,903,770 | 2/1990 | Whigham et al. . |

OTHER PUBLICATIONS

U.S. application No. 08/915,677, Weijand et al, filed Aug. 19, 1997.

*Primary Examiner*—Scott M. Getzow
*Attorney, Agent, or Firm*—Michael J. Jaro; Harold Patton

[57] ABSTRACT

There is provided an output stage for a battery powered implantable device, such as a cardiac pacemaker, for generating biphasic or triphasic pulses, each pulse having at least a prestimulus or poststimulus pulse of a first polarity, and a stimulus pulse of opposite polarity. The output stage provides for charging of a small sized pacing capacitor from the battery through a high rate charge pump only during delivery of a prestim or poststim pulse, and for discharging the pacing capacitor during the stimulus portion of the overall pulse. A fast or high rate capacitive charge pump is used with a controllable high rate clock signal, adjustment of the clock signal being used for controlling the charging rate during the prestim or poststim pulses, thereby allowing for tuning of the parameters of the prestim or poststim pulse portions. The charge pump is enabled only during such charging pulse durations, thereby eliminating the need for a large holding capacitor, and enabling an output stage with a significantly reduced capacitor requirement.

22 Claims, 5 Drawing Sheets

STIMULUS SYSTEM WITH CONTROLLABLE SWITCHED CAPACITOR OUTPUT STAGE

FIELD OF THE INVENTION

This invention relates to battery-driven stimulus generator devices and, more particularly, implantable stimulators such as pacemakers and the like for delivering stimulus pulses for cardiac pacing or other applications.

BACKGROUND OF THE INVENTION

Implantable pacemakers and other implantable stimulus devices must be designed for efficient generation and delivery of stimulus pulses. Such stimulus pulse generation must meet a number of criteria. The generated pulse must be controllable in terms of energy level and other parameters. Typically for pacemakers, the energy level is programmable or adjustable with increments of 0.1 volts between about 0.5 V and 1.5 or 2 V, and within a duration of about 0.1–1.5 ms, so that the pulse energy level can be adjusted with respect to the patient pacing threshold. Further, as discussed in U.S. Pat. No. 4,343,312, which is incorporated herein by reference, it is desirable to deliver a stimulus which minimizes the polarization that results at the electrode where the pulse is delivered. In the pacemaker environment, minimization of such polarization is highly desirable in order to enable enhanced detection of evoked responses, and better detection of other important signal information such as the T-wave. The aforementioned U.S. Pat. No. 4,343,312 discloses a pulse generator for generating a triphasic pulse, comprising positive recharge pulses immediately before and after the negative, or discharging stimulus signal, the recharge pulses being adapted in time duration and amplitude such that the total current delivered at the electrode is substantially zero, thereby minimizing polarization.

Another important feature of a pulse generator output stage is minimization of capacitors. In a typical output stage, such as the referenced triphasic stage, a nominally large holding capacitor of up to about 20 $\mu$F is required in order to hold the desired voltage value which has been obtained by raising the battery voltage through a charge pump. Such a large capacitor not only adds to cost, but presents a larger size which is crucially important in an implantable device such a pacemaker.

Another problem with prior art circuits is that of adjusting the pacing voltage in desirably small voltage steps. A typical prior art pump circuit as found in pacemakers provides for a plurality of different capacitor configurations, each yielding an output voltage which is a different multiple of the battery voltage. However, there is a limit to the number of capacitors that can be utilized for obtaining different voltage values, for cost and space reasons.

Accordingly, there remains a need in the art for an improved output stage for battery-driven devices such as pacemakers, neural stimulators, and the like, which can provide better control of the output pulse parameters and be realized with savings in required capacitors.

SUMMARY OF THE INVENTION

In accordance with the above over-all object, there is provided a switched capacitor output stage for a battery driven stimulus device, which operates without the need for a holding capacitor, and provides for a controllable biphasic or triphasic output pulse.

In a preferred triphasic pulse generator embodiment of this invention, a fast capacitive charge pump is used for transforming the battery voltage to a desired voltage level; the charge pump has a switchable capacitor network which is driven by a high rate clock signal only during the duration of charging pulse portions of an output stimulus pulse. A pacing capacitance or coupling capacitor is connected between the charge pump output and the electrical load, i.e., the heart in a pacemaker. A second switching circuit is utilized for switching the pacing capacitance into a first electrical circuit during a prestim duration, whereby it charges through the load to provide a first polarity prestim pulse; into a second circuit configuration for providing a discharge stimulus pulse; and back to the first charging configuration for a poststimulus duration to provide a poststimulus pulse portion. By enabling the charge pump to be clocked only during charging pulse durations, no holding capacitor is required. Further, control of the clock rate effectively controls the resistance in series with the load during charging, and thus enables control of parameters of the prestim and/or poststim charging pulses.

In another embodiment, the voltage built up during the prestim charging pulse is monitored; when the pacing pulse voltage rises to a predetermined level corresponding to the desired stimulus pulse level, the prestim pulse is terminated and then the stimulus is generated, thereby providing for continuously variable control of the stimulus output voltage level.

DESCRIPTION OF THE PREFERRED EMBODIMENTS

Figure 1A:
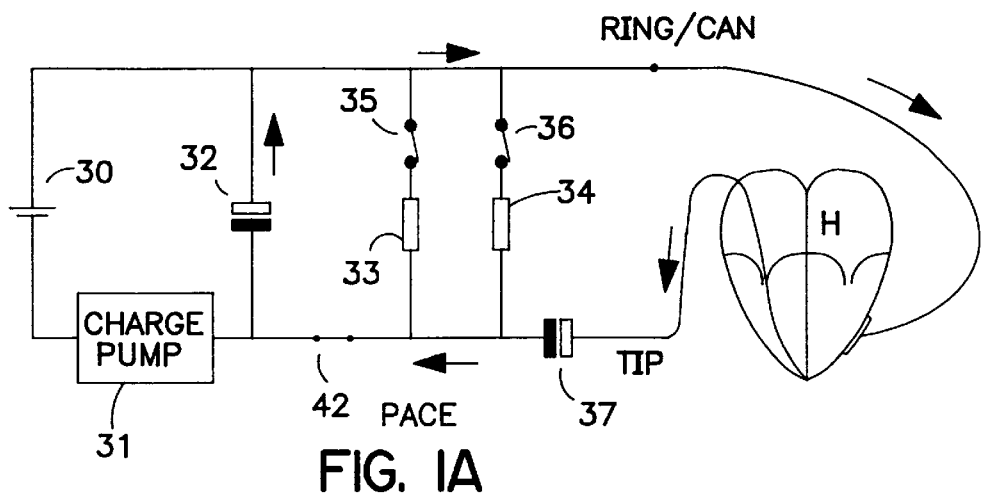
FIGS. 1(a), 1(b) and 1(c) are circuit representations of a prior art triphasic circuit for delivering stimulus pulses to a heart.
Figure 1B:
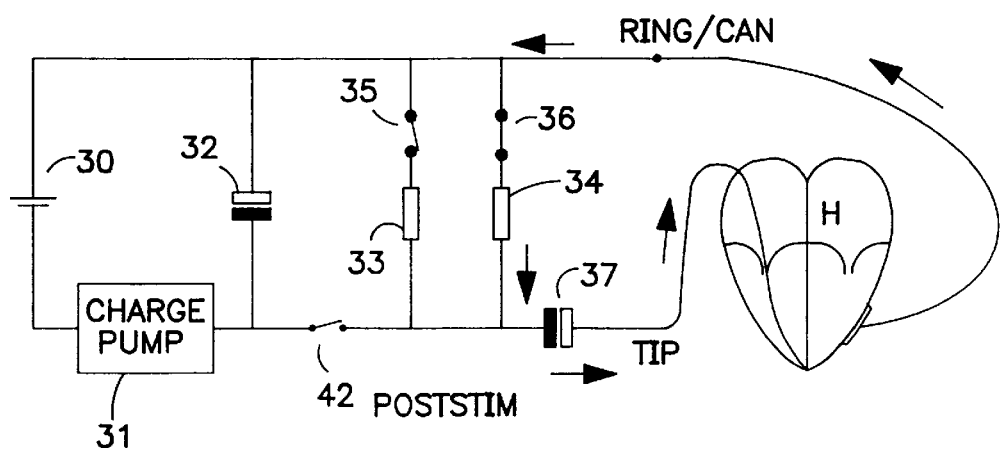
Figure 1C:
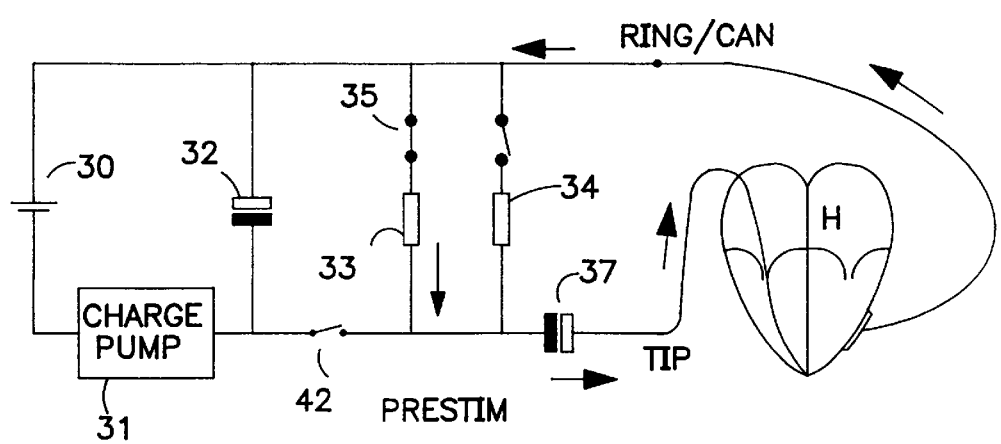
Figure 1D:
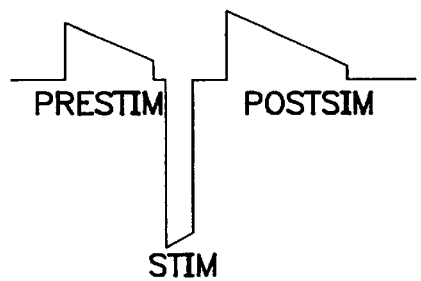
FIG. 1(d) is a timing diagram of a triphasic pulse.
Figure 1E:
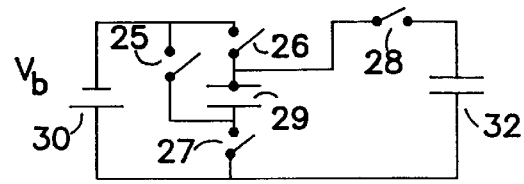
FIG. 1(e) is a circuit diagram of a very simple charge pump.

Referring now to FIGS. 1(a), 1(b) and 1(c), there are shown three configurations of a prior art output stage for generating triphasic output pulses of the form shown in FIG. 1(d). A battery 30 is constantly connected in a first loop with a charge pump 31 and a holding capacitor 32. A holding capacitor in a typical pacemaker application may be about 6.8 $\mu$F; it could be as high as about 20 $\mu$F. The charge pump is any well known charge pump circuit, which comprises a capacitance network and a switching network, the switching network being driven by a clock signal which goes to provide the pumping action. FIG. 1(e) shows a very simplified pump for providing an output voltage of 2 $V_b$. In the simple circuit of FIG. 1(e), a capacitor 29 is switched into different charging and pumping configurations by the switch network. Thus, during the charging half cycle of the clock signal, switches 26 and 27 are closed, while switches 25 and 28 are open; during this time the capacitor charges up to substantially $V_b$. During the next half cycle switches 26 and 27 are open, and switches 25 and 28 are closed, placing the voltage on capacitor 29 in adding series relationship to the battery voltage, thereby delivering a voltage of 2 $V_b$ to holding capacitor 32.

Returning to FIG. 1(a), a first shunt path consists of switch 35 and resistor 33; and a second path consists of resistor 34 and switch 36. A third path through switch 42 and holding capacitor 32 comprises a conductor which leads to the heart H, e.g., through electrodes positioned at the distal end of a pacing lead, and back through pacing capacitor 37.

During the interval between delivery of stimulus pulses, switch 42 is open, and holding capacitor 32 accumulates the required charge and voltage as provided by battery 30 and charge pump 31. During delivery of the negative going stimulus pulse, switches 35 and 36 are opened, and capacitance 32 is discharged directly through the heart via the pacing capacitor 37 and closed switch 42. This results in a charge transfer from holding capacitor to the pacing capacitor and the heart. In contrast, during the prestim pulse (FIG. 1(c)), the pacing capacitor 37 is connected to the heart via resistor 33, and during the poststim pulse (FIG. 1(b)), pacing capacitor 37 is connected to the heart via resistor 34. Each of the prestim and poststim pulses, or pulse portions, results in a discharge of the heart and of capacitor 37. For the prestim pulse, the pulse level is set by the value of resistor 33; for the poststim pulse, the pulse level is set by the value of resistor 34. The basic idea of the tri-phasic pulse is that at the end of the poststim period, the net charge delivered at the electrode is zero, and the polarization is minimized, although the pacing capacitor 37 is not completely discharged. Note that during the prestim period, the discharging of the pacing capacitor is continued, so that the pacing capacitor 37 is fully discharged at the start of the primary stimulus pulse. This procedure is controlled by setting the value of prestim resistor 33 and also by controlling the length, or duration of the prestim.

It is to be noted that with this prior art circuit, charging of holding capacitor 32 is continuous. Also, during delivery of the stimulus pulse, the heart is in series with an effective capacitance equal to the series of capacitance of C32 and C37.

Figure 2A:
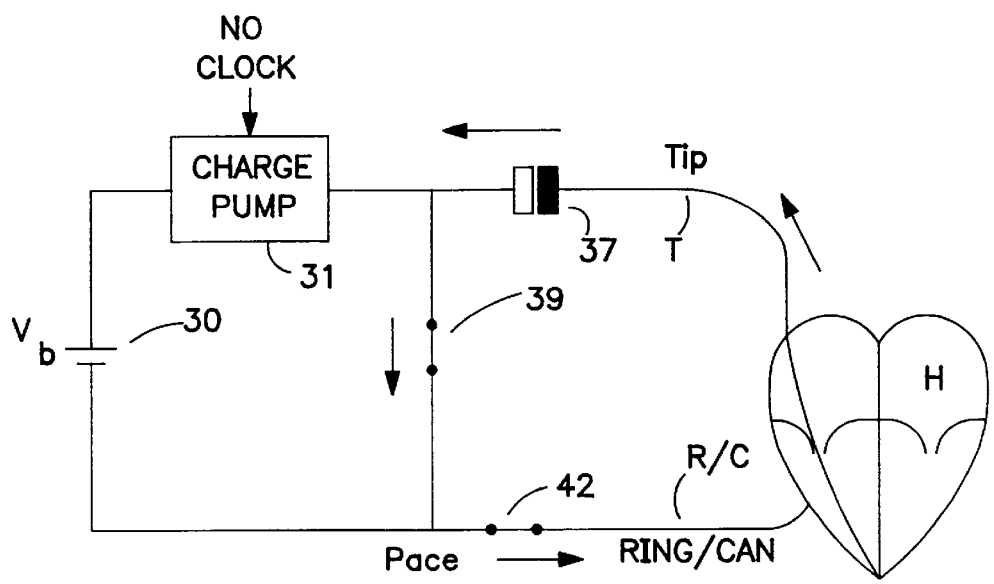
FIGS. 2(a) and (b) are circuit diagrams showing a simplified circuit diagram of a circuit of this invention in the stimulus (pace) mode and in the prestim/poststim mode respectively.
Figure 2B:
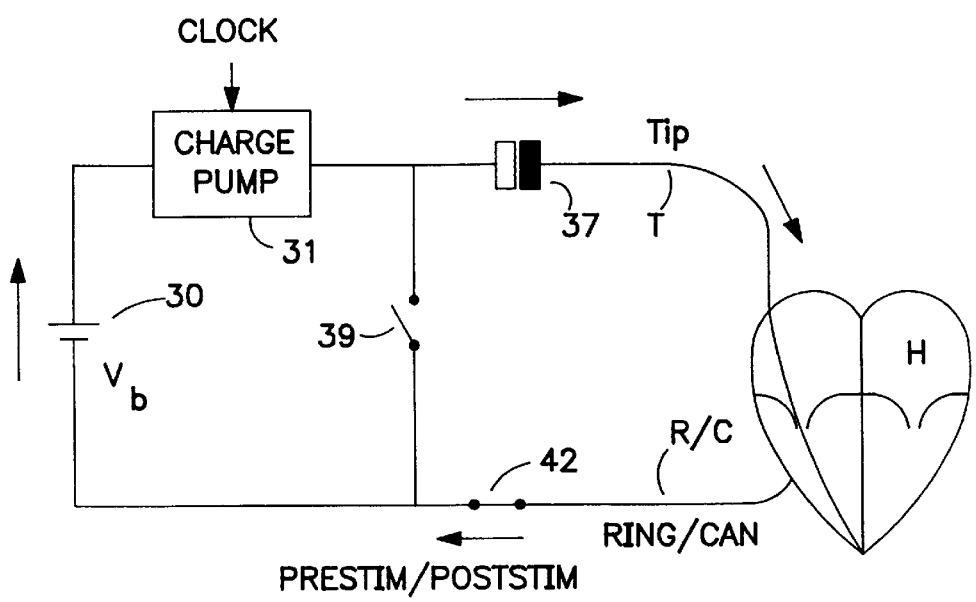

Referring now to FIGS. 2(a) and 2(b), there is shown a simplified circuit diagram of the new output stage of this invention, for generating a triphasic output pulse. As seen, the battery is combined in series with a charge pump 31, for providing a multiple of the battery voltage when the pump is in operation. During time intervals between delivery of stimulus pulses, no clock signal is delivered to the charge pump 31, such that it is effectively disabled; and switch 42 is open. At the time of delivery of the prestimulus pulse, the circuit is switched to the configuration shown in FIG. 2(b), where the clock signal enables the charge pump 31, switch 42 is closed and switch 39 is open. Under these circumstances, the output of the charge pump 31 is delivered through the pacing capacitor 37 in a closed loop to and through the heart. During this prestimulus duration, pacing capacitor 37 charges up, as indicated. At the time of delivering the pacing pulse, the circuit is switched to the configuration shown in FIG. 2(a), wherein the charge pump is not driven by the clock signal, and switch 39 is closed. Under these conditions, the pacing capacitor 37 discharges in the direction of the arrows as shown, delivering the stimulus pulse to the heart. At the end of the stimulus duration, the circuit is switched back to the configuration of FIG. 2(b), and the poststimulus pulse is delivered in the direction shown, with energy being delivered to the charge pump 31, charging pacing capacitor 37 and delivering charge to the heart in the direction shown. A lead L connects the pulses from output stage to the heart, through a tip electrode T and a second electrode R/C, either a ring electrode or the pacemaker can, in a known manner. When no pulse is being generated, switch 42 is open, and the charge pump 31 is not clocked.

From the above, it is seen that in the embodiment of this invention, the pacing energy is transferred to the pacing capacitor and stored there only during the prestim/poststim pulses, while during the stimulus pulse the pacing capacitor is discharged through the heart. During the prestim and poststim periods, the charge pump is driven by a high rate clock signal, to provide a fast pumping action for charging the pacing capacitor 37 and charging the heart. Outside of the prestim and poststim periods, i.e., during the stimulus pulse and during the entire interval between delivery of pulses, the charge pump is not active and is effectively disconnected from the output circuit. It is important to this design that the charge pump runs at a high clock frequency compared to the durations of the prestim and poststim pulse portions. Thus, for prestim and poststim pulses on the order of 3–10 ms, the clock frequency is suitably around 10 kHz, or somewhere in the range of 5–20 kHz, although it could be higher or lower depending upon the application. On the one hand, it is desirable to keep the clock rate low in order to minimize battery drain, but on the other hand, depending upon the characteristics of the heart load, which varies from patient to patient, it may be desirable to use a higher rate. However, for many applications, the clock rate can be at least 5×1/D, where D is the pulse portion duration; a clock rate in the range of 1–20 kHz should be suitable for most applications, although there is no upper limit to the clock rate.

From a low frequency point of view, the charge pump 31 behaves like an ideal voltage circuit of nVb, where n does not need to be an integer, in series with a switched capacitor resistor $R_{SW}$, according to the following:

$$R_{SW}=1/(f_{SW} \times C_{eff}),$$

where $f_{SW}$ is the charge pump clock frequency and $C_{eff}$ is the effective pump capacitance. From this formula, it can be seen that, for a given value of $C_{eff}$, the value of $R_{SW}$ can be controlled by changing the charge pump clock frequency, thereby changing the effective resistance in series with the pacing capacitor and heart during delivery of prestim and poststim pulse portions. In this manner, control of the clock frequency can be used to control the current value of the prestim and poststim pulses, instead of having to use values fixed by resistors, as in the prior art circuit. Of course, the charge pump itself can use different pump capacitor configurations, resulting in different values of $C_{eff}$, for additional control of the effective resistance $R_{SW}$.

Figure 3:
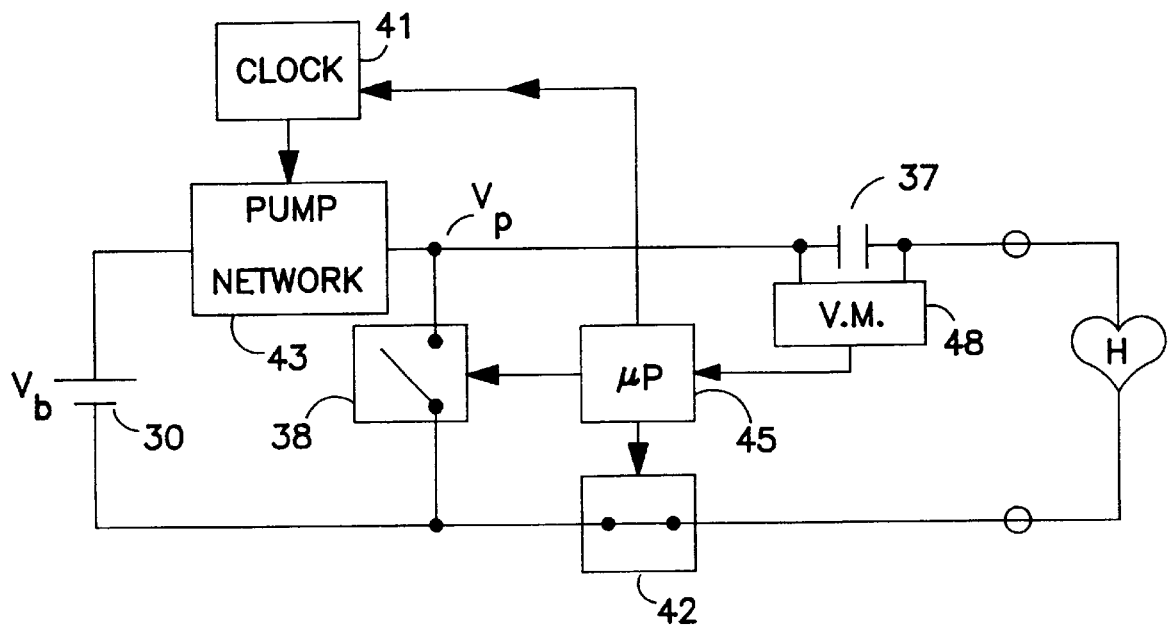
FIG. 3 is a circuit diagram of the output stage circuit of this invention with microprocessor control.

Referring now to FIG. 3, there is shown a circuit diagram of an output stage in accordance with this invention, which is further adapted to provide a variable control of the stimulus voltage level. The circuit of FIGS. 2(a) and 2(b) is modified by further showing a microprocessor, or other control block 45, which carries out a number of logic and timing functions, as discussed further in connection with FIG. 4. As illustrated, control signals from block 45 control the switching of switches 38 and 42. Also, the microprocessor generates control signals which are inputted into clock circuit 41, both for controlling the clock to be on or off, and to control the rate of the clock. The output of the clock, when it is enabled, is transferred to operate the pump switching network 43. Of course, when the clock generator 41 is disabled, there is no clock signal for switching the charge pump switches, such that charge pump network 43 is essentially disabled. As further seen in FIG. 3, a circuit 48 is used to determine when the voltage across pacing capacitor 37 has reached a predetermined value, i.e., a desired value for the voltage amplitude of the stimulus pulse. When this predetermined threshold level is reached, a signal is transferred from circuit 48 to the microprocessor, which then can control switching of the output stage from the prestim arrangement to the stimulus arrangement. This enables setting of the pacing voltage over a substantially continuous voltage range, such that is is not necessary to provide a great number of pump capacitor capacitance configurations. Also, the signal from the voltage detector block 48 can be used to enable adjustment of the time duration of both the prestim and poststim pulses, and/or the value of $R_{SW}$ during prestim and poststim, to achieve minimal polarization. Thus, the microprocessor in this mode is used to balance out the charge across pacing capacitor 37 from the start of the prestim pulse to the end of the poststim pulse, so as to achieve a substantially net zero overall charge transfer as desired for minimizing polarization. Further, the measurement circuit can be used to monitor the charge leakage from pacing capacitor 37 between pulses, i.e., during the pacing interval. Thus, if the voltage across capacitor 37 drops too much between pace pulses, the charge pump is switched on earlier than usual, so that the prestim period is extended in order to compensate for the charge leakage.

Figure 4:
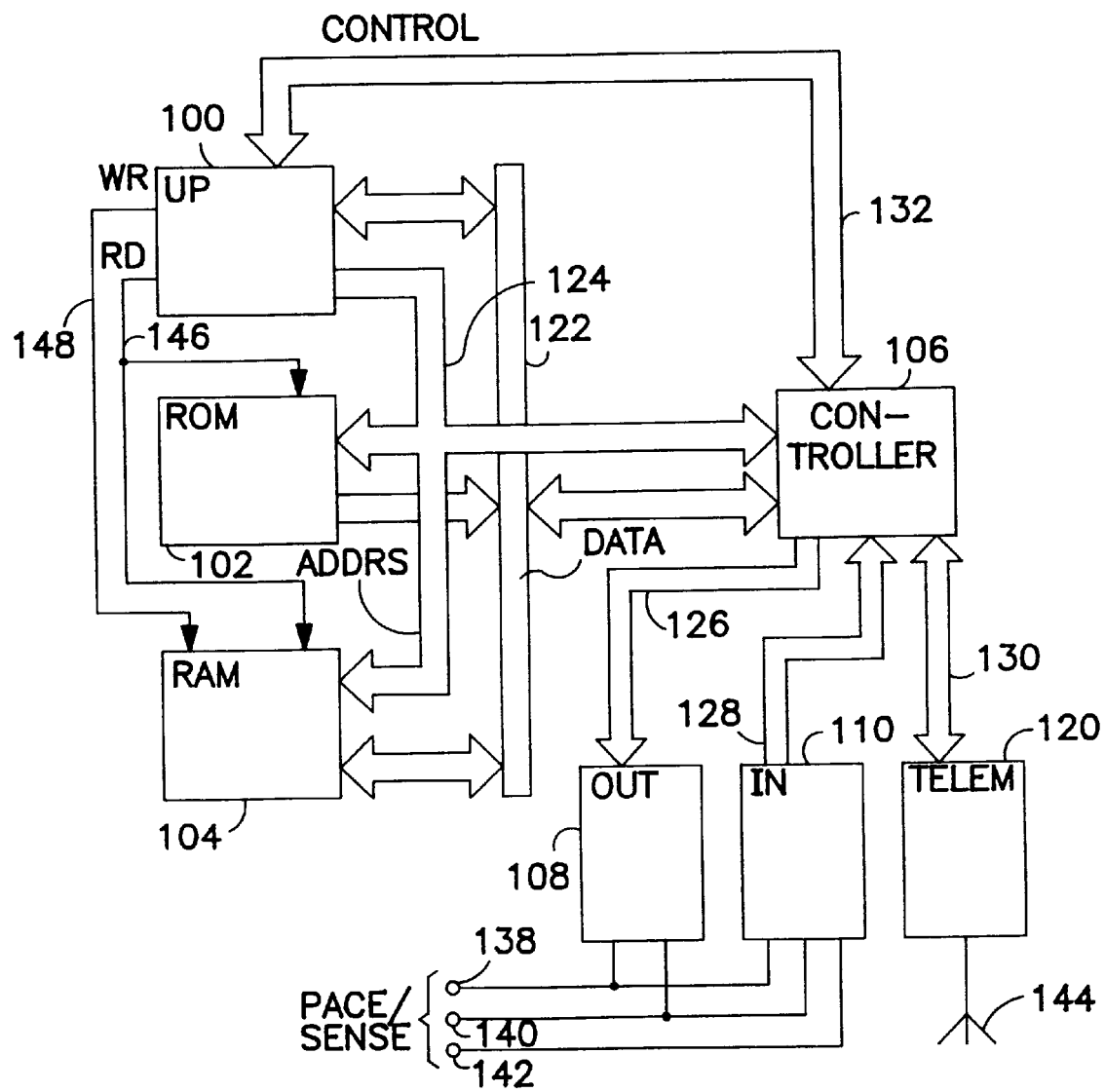
FIG. 4 is a block diagram showing the primary components of the pacemaker system which incorporates the output stage of this invention.

FIG. 4 is a functional block diagram of an implantable pacemaker of the type in which the present invention may be practiced. The disclosed embodiment takes the form of a microprocessor controlled device. However, it is believed that the invention might usefully be practiced in other types of devices, including those employing dedicated digital circuitry, and perhaps even in devices comprised primarily of analog timing and control circuitry. As such, FIG. 4 should be considered exemplary, rather than limiting with regard to the scope of applications of the present invention. While the invention is disclosed as embodied in a pacemaker, it is equally applicable to incorporation in a cardioverter, or combined cardioverter pacemaker, or even cardioverter defibrillator pacemaker. While the following discussion of FIG. 4 assumes a single chamber ventricular pacing system, it is to be understood that the invention is applicable to dual chamber systems and multi-chamber systems. For dual or multiple chamber systems, the savings due to being able to use smaller capacitors are achieved for each channel.

The primary elements of the apparatus illustrated in FIG. 4 are microprocessor 100, read only memory 102, random access memory 104, a digital controller 106, input and output amplifiers (stages) 110 and 108 respectively, and a telemetry/programming unit 120.

Read only memory 102 stores the basic programming for the device, including the primary instructions set defining the computations performed to derive the various timing intervals performed by the device. Random access memory 104 serves to store the values of variable control parameters, such as programmed pacing rate, pulse widths, pulse amplitudes, and so forth, which are programmed into the device by the physician. Reading from random access memory 104 and read only memory 102 is controlled by RD-line 146. Writing to random access memory 104 is controlled by WR-Line 148. In response to a signal on RD-Line 146, the contents of random access memory 104 or read only memory 102 designated by the then present information on address bus 124 are placed on data bus 122. Similarly, in response to a signal on WR-line 148, information on data bus 122 is written into random access memory 104 at the address specified by the information on address bus 124.

Controller 106 performs all of the basic timing and control functions of the device. Controller 106 includes at least one programmable timing counter, initiated on ventricular contractions, paced or sensed, for timing out intervals thereafter. This timing counter is used to define the escape intervals for timing generation of pace pulses, and for timing the respective durations of the charge and recharge pulse portions. Controller 106 triggers output pulses from output stage 108 as discussed below, and it generates interrupts on control bus 132 for cyclically waking microprocessor 100 from its sleep state to allow it to perform the required functions. Output circuit 108 is coupled to electrodes 138 and 140 which are employed both for delivery of pacing pulses and for sensing of cardiac signals. Electrode 138 is typically located on the distal tip end of an endocardial lead and is typically placed in the apex of the right ventricle; for atrial mode pacing, of course, it is placed in the patient's atrium. Electrode 140 is preferably a ring electrode, as used with a bipolar lead. Electrode 142 represents the pacemaker housing, which may be used as the indifferent electrode for selected unipolar pacing and/or sensing operations, as discussed below. Output circuit 108 is controlled by controller 106 through bus 126 to determine the time, amplitude and pulse width of the pulse to be delivered and to determine which electrode pair will be employed to deliver the pulse.

Sensing of cardiac signals, e.g., QRS and T-waves, is done by input amplifier circuitry 110, which receives sensed signals from electrodes 138, 140, and/or 142. Signals indicating the occurrences of natural ventricular contractions, and paced ventricular contractions as well as T-waves, are provided to the controller 106 via bus 128. Controller 106 passes data indicative of the occurrence of such ventricular signals to microprocessor 100 via control bus 132, for performance of all necessary calculations.

External control of the implanted device is accomplished via telemetry/control block 120, which allows communication between the implanted device and an external programmer, (not shown). Radio communication is typically employed via antenna 124. Appropriate telemetry/programming systems are disclosed in U.S. Pat. No. 4,401,120, issued to Hartlaub et al., U.S. Pat. No. 4,556,063, issued to Thompson et al., and U.S. Pat. No. 4,550,370, issued to Baker, all of which are incorporated herein by reference in their entireties. However, any conventional telemetry/programming circuitry is believed workable in the context of the present invention. Information entering the pacemaker from the programmer is passed to controller 106 via bus 130. Similarly, information from the pacemaker is provided to the telemetry block 120 via bus 130, for transmission to the external programmer.

Figures 5A, 5B:
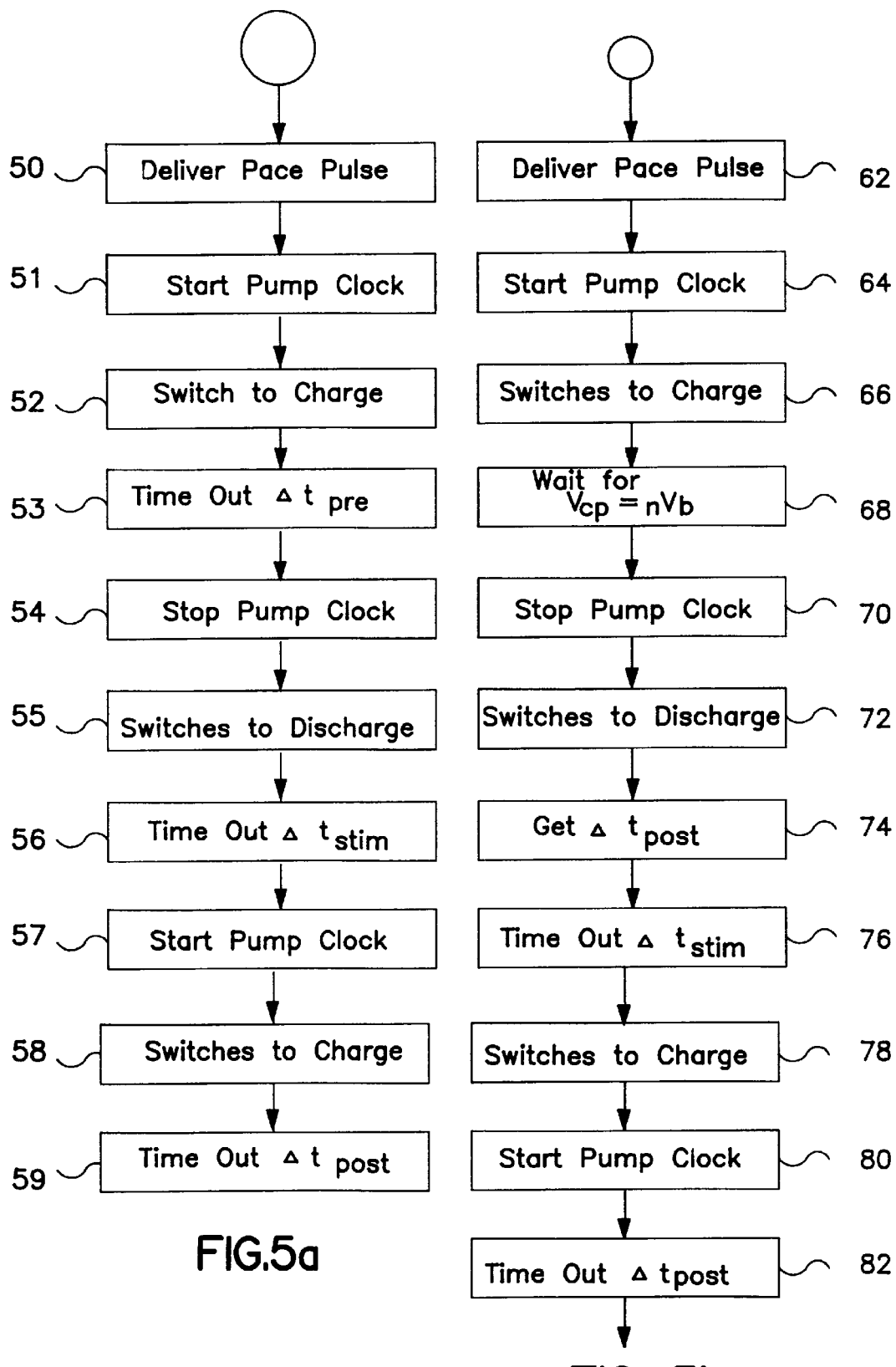
FIG. 5(a) is a flow diagram of the logic steps for controlling generation of a triphasic stimulus pulse in accordance with the output stage of this invention.
FIG. 5(b) is a flow diagram of the control steps taken for controlling the voltage level of the stimulus of the discharge portion of a triphasic pulse generated with the output stage of this invention.

Referring now to FIG. 5(a), there is illustrated a flow diagram of the logic steps taken in generating a triphasic stimulus pulse in accordance with the output stage of this invention. At block 50, the logic and timing circuitry has determined that it is time to deliver a pace pulse. In a pacemaker embodiment, this means the appropriate escape interval has timed out, such that a pacing pulse is to be delivered to a heart chamber. At 51, the pump clock (shown as 41 in FIG. 3), is started, thereby enabling the charge pump network. Concurrently, at 52 the control switches to a charge mode, i.e., as seen in FIG. 2(b). The routine then waits for a time duration of $\Delta t_{pre}$, the duration of the prestim pulse, as illustrated at 53; after timeout of the prestim duration, at 54 the pump clock is stopped, and at 55 the circuit is switched to the discharge arrangement, as seen in FIG. 2(a). Then, at 56, the stimulus duration, $\Delta t_{stim}$ is timed out. At the end of the stimulus duration, the pump clock is again started at 57, and at 58 the output stage is switched back to the charge configuration as shown in FIG. 2(b). These conditions are maintained while the poststim duration, $\Delta t_{post}$ is timed out as shown at 59, whereafter the charge pump is turned off and the routine exits; the pacemaker waits for a signal to deliver the next pacing pulse.

Referring now to FIG. 5(b), there is shown a modification of the sequence of FIG. 5(a), wherein voltage across the pacing capacitor is monitored in order to set the voltage of the stimulus pulse to a predetermined level. At 62, it is determined that a pace pulse is to be delivered. At 64 the pump clock is started, and at 66 the control switches the circuit to the charge mode. At 68, the routine waits and watches the signal from volt meter circuit 48, and determines when the voltage across the pacing capacitor has reached a desired value, illustrated as $nV_b$. When this happens, signaling the time for delivery of the stimulus pulse, at 70 the pump clock is stopped, and at 72 the circuit is switched to the discharge configuration of FIG. 2(a). Then, at 74 the poststim duration is calculated so as to combine optimally with the prestim duration, and at 76 the stimulus duration is timed out. After timing out of the stimulus duration and delivery of the stimulus pulse, at 78 the circuit is switched back to the charge configuration, and the pump clock is started at 80. At 82, the routine waits while the poststim pulse is delivered, and then exits.

It is to be noted that during the prestim and poststim durations, the fast charge pump draws a current in the milli-ampere range from the battery. As a consequence, it is important to use a battery with low internal resistance which can provide such high currents to be drawn during these intervals, without significant adverse effect on the battery voltage as used for the remainder of the pacemaker. Otherwise, a significantly large battery voltage buffer capacitor is required, which would offset one of the primary advantages of this invention. While conventional $Li/I_2$ batteries cannot be used without such a large buffer capacitor due to their high internal impedance, new battery techniques are becoming available which provide the desired low internal resistance. Examples of such new batteries include those characterized as $Li/MnO_2$; Li/CSVO; $Li/(CF)_x$; $Li/(CF)_x$—CSVO.

It is to be seen that the invention as disclosed eliminates the need for a holding capacitor, which can save at least 50% in output stage capacitor cost. Furthermore, the fact that the effective capacitor in series with the heart during the stimulus is the pacing capacitance only, permits the use of smaller capacitance values. For example, in current pacemakers made by the assignee of this invention, both the holding capacitance and pacing capacitance have values of 6.8 μF, which achieves an effective pacing capacitance of 3.4 μF. Consequently, with the circuit of this invention, the capacitance requirement is only 3.4 μF, enabling the use of a standard pacing capacitance of 3.3 μF. This reduction in the pacing capacitance, together with elimination of the holding capacitor, results in an effective 75% reduction of the volume needed for the capacitors per pacing channel, given the same capacitance-per-volume ratio. There is a corresponding savings in cost, due to the fact that the price of tantalum capacitors normally is substantially proportional to the capacitance value. Further, by providing control of the effective resistance $R_{SW}$, through controlling the charge pump clock frequency, there is provided a greater flexibility in modifying the parameters of the prestim and poststim pulses, so as to provide more accurate optimization of polarization.

Although the invention has been disclosed by illustrating generation of triphasic pulses, it is to be understood that the output stage can also be used to generate biphasic pulses, i.e., a combined pulse that incorporates a stimulus pulse portion followed by a recharge duration. In the case of a biphasic output pulse circuit, the pacing capacitance needs to be completely recharged at the end of the stimulus discharge, which in turn can be optimized by controlling the value of $R_{SW}$ through adjustment of the charge pump clock frequency.

We claim:

1. An output stage circuit for receiving power from a DC voltage source, and for delivering output pulses to a load, comprising:

a fast capacitive charge pump, having an input connected to said voltage source, switchable capacitive pump means for providing an amplified voltage, first switch means for switching said capacitive pump means at a controllable high switching rate, and a pump output for providing said amplified voltage;

a pace capacitance connected to said pump output and to said load;

second switching means for switching said pace capacitance into a first electrical circuit for a first predetermined duration, whereby it discharges through said load to provide a first polarity pulse to said load; and into a second circuit for a second predetermined duration, whereby it charges from said voltage source and said charge pump through said load to provide a second polarity pulse of duration D to said load, pump activation means for activating said charge pump to provide an output substantially only when said pace capacitance is switched into said second circuit during duration D; and said first switch means has rate means for setting said high switching rate much greater than 1/D Hz.

2. The output stage circuit as described in claim 1, wherein said DC voltage source comprises a battery, and said load is a heart to which pacing pulses are delivered by said output stage circuit.

3. The output stage circuit as described in claim 1, wherein said rate means comprises means for controlling said switching rate to be greater than 5/D Hz.

4. The output stage circuit as described in claim 1, wherein said second duration is at least about 0.1 ms, and said switching rate is greater than about 50 kHz.

5. The output stage circuit as described in claim 1, comprising rate control means for controlling said switching rate during said second duration to provide a predetermined voltage level of a said second polarity pulse.

6. The output stage circuit as described in claim 1, wherein said capacitive pump means comprises a plurality of capacitors, and said first switching means comprises means for connecting said plurality of capacitors at said switching rate to provide respective amplified voltage values.

7. The output stage circuit as described in claim 1, comprising control means for controlling the operation of said second switching means, said control means having timing means for enabling said second switching means to switch said pace capacitance into and out of one of said first and second circuits so as to produce pace pulses of predetermined durations.

8. The output stage circuit as described in claim 1, wherein said control means comprises biphasic means for enabling switching of said pace capacitance serially into said first circuit for a first predetermined duration and into said second circuit for a second predetermined duration, thereby providing a biphasic output pulse.

9. The output stage circuit as described in claim 1, wherein said control means comprises triphasic means for enabling switching of said pacing capacitance serially into said second circuit, then said first circuit, and then said second circuit for respective predetermined prestim, stim and poststim durations, thereby providing a triphasic output pulse.

10. The output stage circuit as described in claim 1, wherein said first switching means comprises controllable clock means for generating a clock signal of controllable rate, and pulse control means for controlling said clock means during a delivered pulse output, thereby controlling at least one parameter of said delivered pulse output.

11. A cardiac pacemaker for generating pacing pulses, comprising:

a battery source of power, providing a voltage output of Vb;

output terminals, for connection to a pacing lead for delivery of pacing pulses to an electrical load in the form of a patient's heart;

output capacitive means connected to one of said terminals, for capacitively coupling said pacing pulses to said heart load;

switching capacitance voltage pump means connected to receive power from said battery, for generating a voltage output of about nVb when enabled;

first pulse control means for enabling said pump means only during a said pacing pulse and for connecting said output capacitive means in a charging path with said pump means for a predetermined charging duration during a said pacing pulse, thereby delivering a charging pulse through said output terminals for said charging duration;

said first pulse control means comprising clock means for clocking said pump means at a high rate relative to said charging duration; and second pulse control means for connecting said output capacitive means in a discharging path with said heart for a predetermined discharging duration, thereby delivering a discharging pulse through said output terminals for said discharging duration.

12. The pacemaker as described in claim 11, comprising timing means for generating timing signals for control of said first and second control means so as to generate combined pacing pulses made up of at least a discharging pulse and a charging pulse.

13. The pacemaker as described in claim 12, wherein said first pulse control means comprises pump enabling means for enabling said pump means to generate a voltage output substantially only during a said charging pulse.

14. The pacemaker as described in claim 13, wherein said timing means comprises triphasic means for generating timing signals for generating a triphasic combined pulse having a first charging pulse, a second discharging pulse, and a third charging pulse.

15. The pacemaker as described in claim 11, comprising a clock generator for generating a high rate switching signal for switching said capacitive pump means at high rate relative to said charging duration.

16. The pacemaker as described in claim 15, comprising rate control means for controlling the rate of said clock switching signal during a charging duration.

17. The pacemaker as described in claim 11, comprising a clock generator for generating a switching signal having a rate greater than about 10 kHz for switching said capacitive pump means.

18. A circuit in an implantable device powered by a battery type power source, said circuit having output terminals for delivering output pulses to an electrical load, comprising:

a coupling capacitor connected to one of said output terminals;

timing means for generating an overall pulse duration which has at least one charging duration and a discharging duration;

transfer means for taking energy from said source and concurrently transferring charge from said source to said coupling capacitor only during a said charging duration; and discharge means for discharging said coupling capacitor through said load during said discharge duration, thereby generating an output pulse having a first polarity pulse portion during said charging duration and an opposite plurality pulse portion during said discharge duration.

19. The device as described in claim 18, wherein said timing means comprises triphasic means for generating a stimulus discharge duration, a prestim duration which precedes said stimulus duration and a poststim duration which follows said stimulus duration, whereby said first polarity pulse portion comprises said prestim duration and said poststim duration.

20. The device as described in claim 18, wherein said transfer means comprises a variable rate capacitive pump circuit, and enabling means for enabling said pump circuit to transfer energy to said coupling capacitor during a said charging duration.

21. The device as described in claim 20, wherein said timing means comprises means for generating said output pulses at a predetermined rate, and said transfer means comprises amplitude means for controlling the amplitude of said first and second pulse portions.

22. The device as described in claim 21, wherein said enabling means comprises a clock circuit which clocks said pump circuit at a controllable clock rate, and wherein said amplitude means comprises means for adjusting said each of said amplitudes by adjusting said clock rate during said first and second pulse portions.

* * * * *